(12) United States Patent
Beckmann et al.

(10) Patent No.: US 8,971,484 B2
(45) Date of Patent: Mar. 3, 2015

(54) HIGH SPEED, SMALL FOOTPRINT X-RAY TOMOGRAPHY INSPECTION SYSTEMS, DEVICES, AND METHODS

(71) Applicant: XinRay Systems Inc., Research Triangle Park, NC (US)

(72) Inventors: Moritz Beckmann, Cary, NC (US); Frank Sprenger, Cary, NC (US); Yuan Cheng, Durham, NC (US); Jianping Lu, Chapel Hill, NC (US); Derrek Spronk, Raleigh, NC (US); George Zarur, Gainesville, FL (US); Otto Z. Zhou, Chapel Hill, NC (US)

(73) Assignee: XinRay Systems Inc, Research Triangle Park, NC (US)

( * ) Notice: Subject to any disclaimer, the term of this patent is extended or adjusted under 35 U.S.C. 154(b) by 308 days.

(21) Appl. No.: 13/683,633

(22) Filed: Nov. 21, 2012

(65) Prior Publication Data
US 2013/0170611 A1 Jul. 4, 2013

Related U.S. Application Data

(60) Provisional application No. 61/629,612, filed on Nov. 22, 2011.

(51) Int. Cl.
*G01F 1/66* (2006.01)
*G01N 23/04* (2006.01)
(Continued)

(52) U.S. Cl.
CPC .............. *G01N 23/046* (2013.01); *G01V 5/005* (2013.01)
USPC ................. 378/51; 378/62; 378/57; 378/122; 378/136; 378/147

(58) Field of Classification Search
CPC .... G01N 23/046; G01N 23/04; G01N 23/087; G01N 23/20083; G01N 23/203; A61B 6/4028; A61B 6/032; A61B 6/405; A61B 6/4064; A61B 6/4085; A61B 6/466; A61B 6/482; A61B 6/502; A61B 6/542; B29C 33/42; B29C 33/302; B29C 33/3842; B29C 39/021; B29C 39/34

USPC ......... 378/9, 57, 122, 136, 62, 114, 116, 134, 378/146, 147, 154, 19, 21, 25, 51, 56, 87; 382/131, 195
See application file for complete search history.

(56) References Cited

U.S. PATENT DOCUMENTS 5,940,468 A * 8/1999 Huang et al. .................... 378/57
6,018,562 A * 1/2000 Willson ............................ 378/9
(Continued)

FOREIGN PATENT DOCUMENTS

CN 1833299 A † 9/2008
CN 101641589 A † 2/2010
(Continued)

OTHER PUBLICATIONS

Sidky et al., "Image reconstruction in circular cone-beam computed tomography by constrained, total-variation minimization," Phys. Med. Biol, 2008, pp. 4777-4807, vol. 53, IOP Publishing, United Kingdom.
(Continued)

*Primary Examiner* — David A Vanore
(74) *Attorney, Agent, or Firm* — Jenkins, Wildon, Taylor & Hunt, P.A.

(57) ABSTRACT

The present subject matter relates to inspection systems, devices and methods for x-ray inspection of objects. A conveyor can move an object to be inspected through an inspection zone along a direction of travel, one or more multibeam x-ray source arrays can provide multiple collimated x-ray beams through the inspection zone along a direction substantially perpendicular to the direction of travel, and one or more x-ray detector arrays can detect x-ray beams passing through the inspection zone from the x-ray source array. X-ray signals detected by the x-ray detector array can be recorded to form multiple x-ray projection images of the object, and the multiple x-ray projection images can be processed into three-dimensional tomographic images of the object.

20 Claims, 13 Drawing Sheets

(51) Int. Cl.
*G06K 9/46* (2006.01)
*G01V 5/00* (2006.01)

(56) References Cited

U.S. PATENT DOCUMENTS

| | | | |
|---|---|---|---|
| 6,236,709 B1 * | 5/2001 | Perry et al. | 378/57 |
| 6,553,096 B1 | 4/2003 | Zhou | |
| 7,141,812 B2 * | 11/2006 | Appleby et al. | 250/505.1 |
| 8,155,262 B2 | 4/2012 | Zhou | |
| 8,189,893 B2 | 5/2012 | Zhang | |
| 8,447,013 B2 * | 5/2013 | Sprenger et al. | 378/122 |
| 2004/0240616 A1 † | 12/2004 | Qiu | |
| 2005/0276468 A1 | 12/2005 | Ying et al. | |
| 2007/0147585 A1 | 6/2007 | Eilbert et al. | |
| 2007/0206726 A1 * | 9/2007 | Lu et al. | 378/146 |
| 2008/0043917 A1 * | 2/2008 | Oreper et al. | 378/116 |
| 2008/0069420 A1 † | 3/2008 | Zhang | |
| 2008/0095298 A1 * | 4/2008 | Shefsky | 378/2 |
| 2008/0304622 A1 * | 12/2008 | Morton | 378/51 |
| 2010/0034450 A1 * | 2/2010 | Mertelmeier | 382/131 |
| 2010/0239064 A1 * | 9/2010 | Zhou et al. | 378/9 |
| 2011/0142316 A1 * | 6/2011 | Wang et al. | 382/131 |
| 2011/0206179 A1 * | 8/2011 | Bendahan | 378/19 |

FOREIGN PATENT DOCUMENTS

| | | |
|---|---|---|
| KR | 10-2006-0008146 | 1/2006 |
| WO | 2009115982 A1 † | 9/2009 |
| WO | WO 2013/078344 | 5/2013 |

OTHER PUBLICATIONS

International Search Report and Written Opinion for Application No. PCT/US2012/066299 dated Feb. 28, 2013.

Z. Tian et al., "Edge-preserving algorithm," Phys. Med. Biol. 56 (2011) 5949.

* cited by examiner
† cited by third party

HIGH SPEED, SMALL FOOTPRINT X-RAY TOMOGRAPHY INSPECTION SYSTEMS, DEVICES, AND METHODS

PRIORITY CLAIM

This application claims the benefit of and priority to U.S. Provisional Patent Application Ser. No. 61/629,612, filed Nov. 22, 2011, the disclosure of which is incorporated by reference herein in its entirety.

GOVERNMENT INTEREST

Certain aspects of the presently disclosed subject matter were developed with U.S. Government support under DHS Science and Technology Directorate contract HSHQDC-09-C-00169. Thus, the U.S. Government has certain rights in the presently disclosed subject matter.

TECHNICAL FIELD

The subject matter disclosed herein relates generally to x-ray imaging. More particularly, the subject matter disclosed herein relates to x-ray inspection systems, devices and methods.

BACKGROUND

Passengers travelling on commercial air planes in the United States and other countries have to undergo a security screening at the airport. All baggage travelling with the passenger is also checked. Two types of passenger luggage are distinguished: carry-on luggage that stays with the passenger at all times and checked-in luggage that is handled by the airline. For carry-on luggage, security screening is conducted as quickly as possible in an effort to limit the amount of time it takes for passengers to pass into the airport terminal. As a result, the systems used at the checkpoint are fairly limited because they usually generate only a limited number of projection views (less than 10 views) of the object for visual inspection by a trained human operator. The operator is inspecting the two-dimensional (2D) images for contraband such as weapons or explosives. Because of the limited number of views, objects are usually overlapping in the image making the identification of threats a difficult task for operators and also for software algorithms.

In contrast, for checked baggage, advanced explosion detection systems (EDS) are used that produce high resolution three-dimensional (3D) images and have built in threat detection algorithms that search for hidden contraband automatically. Specifically, x-ray computed tomography (CT) scanners have been used in airports for screening checked baggage to detect whether explosives or other contraband are present within the items. Conventional CT baggage scanners rotate a single-beam x-ray tube and a curved detector in a circular gantry rapidly around a center axis to obtain the 700 to 1,000 2D views needed for 3D reconstruction by the filtered back-projection (FBP) method. In such a system, the baggage items are carried on top of a conveyor belt placed near the central axis of rotation (Z axis), along which the conveyor belt moves as the gantry is rotating. The Z travel length of the baggage irradiated by the x-rays during each rotation is proportional to the moving speed of the conveyor belt and the time period of the rotation of the gantry that holds the x-ray source and detector array. For instance, a state-of-the-art rotating gantry CT may complete two to four revolutions per second.

Conventional CT baggage scanners typically utilize a fan beam in the x-y plane and a single row detector, limiting the volume resolution. Another alternative is to utilize multi-row detectors and sophisticated cone-beam image reconstruction algorithms, which can, in principle, offer a finer volume image reconstruction. Nevertheless, a conventional high throughput CT scanner necessitates a fast-rotating gantry to minimize the baggage travel in Z direction during each rotation of the gantry.

This fast rotation creates several reliability and imaging problems, however. For instance, these rotating gantries are characterized by a large, heavy rotating ring that requires significant space and is highly susceptible to breakdowns caused by the high G forces generated by its rotation. The resulting mechanical wear and tear causes high down-time and necessitates expensive maintenance. The G forces also limit scanning speed, thereby reducing throughput capacity. Furthermore, outside the isocenter, the fast rotation of the gantry causes motion-induced blurring, and this blurring increases as the ball bearings supporting the gantry wear down. Such blurring has been recognized as a leading cause of false alarms. The TSA has reported that the cost of the second and third tier inspection procedures to resolve false alarms costs several hundred million dollars annually.

Accordingly, a stationary gantry CT system that can reduce or eliminate the drawbacks associated with a rotating gantry and that can be built and arranged in a custom geometry to fit the optimum arrangement for the objects being inspected would be advantageous.

SUMMARY

In accordance with this disclosure, inspection systems, devices and methods for x-ray inspection of objects are provided. In one aspect, a computed tomography inspection system is provided and can comprise a conveyor configured to move an object to be inspected through an inspection zone along a direction of travel, one or more multibeam x-ray source arrays operable to provide multiple collimated x-ray beams through the inspection zone along a direction substantially perpendicular to the direction of travel, and an x-ray detector array configured to detect x-ray beams passing through the inspection zone from the x-ray source array. An electronic controller can be operable to electronically turn on and turn off individual x-ray beams from the x-ray source array according to a preprogrammed pattern, a signal processing unit can be operable to record corresponding x-ray signals detected by the x-ray detector array and to form multiple x-ray projection images of the object, and a data processor unit can be operable for processing the multiple x-ray projection images into three-dimensional tomographic images of the object.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which.

DETAILED DESCRIPTION

In recent years, multibeam field emission x-ray (MBFEX) sources based on carbon nanotube (CNT) field emission have been developed that provide multiple focal spots (i.e., source elements) in a single x-ray tube housing. For example, linear modules with a number of focal spots up to 75 or more are available with currents of tens of mA at 160 kV, although there are no theoretical limits on the number of source elements, and x-ray tubes with hundreds of individual source elements have been made. Other exemplary systems and methods are disclosed in co-pending U.S. patent application Ser. No. 13/069,286, which was filed Mar. 22, 2011, the disclosure of which is incorporated herein in its entirety.

Regardless of the specific configuration, these modules can be installed in a security inspection system to provide multiple x-ray views. Such modular multibeam technology enables a stationary gantry CT system that eliminates the drawbacks discussed hereinabove associated with a rotating gantry and can be built and arranged in a custom geometry to fit the optimum arrangement for the objects being inspected. Because the x-ray projection data from different viewing angles are generated by electronically scanning the multibeam x-ray tube, scanning speed is not limited by the speed of mechanical rotation of a bulky gantry. Instead, the constraining factor becomes the speed by which the x-ray image data can be transferred from the detectors, enabling much faster CT scans and increased throughput. Equivalent scanning speed of 40 revolutions per second is readily available. This faster scanning speed translates into smaller voxel size along the Z direction, which results in higher resolution than traditional scanners and therefore improved probability of detection. Further, arranging the x-ray tubes in an array customized to fit the scanned objects saves significant space, and eliminating the rotating gantry reduces total system weight and power consumption.

Using systems and methods according to the subject matter disclosed herein, the density and effective atomic number of the voxels in the 3D image can be determined, and segmentation according to shape and material can be done. A threat detection algorithm can search the segmented 3D image for contraband and dangerous or suspicious objects based on shape and material. In the simplest case, the image data can be displayed on a monitor for manual inspection by a human operator, and suspicious regions or objects can be highlighted. Furthermore, automated-threat detection software can work without human supervision and only alert or alarm human operators if a threat is found. As a result, the systems and methods disclosed herein can be used at passenger checkpoints for carry-on baggage inspection or in another embodiment for checked-in baggage.

Figure 1:
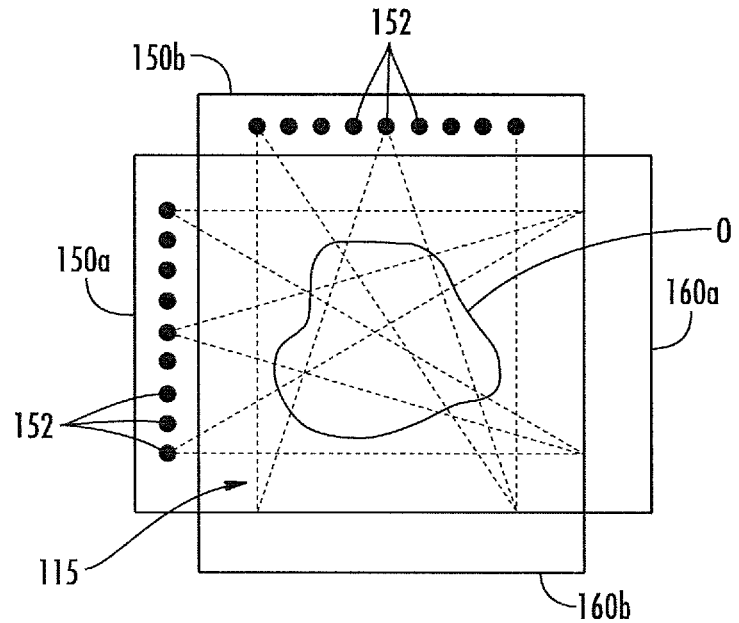
FIG. 1 is a schematic view illustrating an x-ray inspection system according to an embodiment of the presently disclosed subject matter.

Specifically, for example, FIG. 1 illustrates a schematic illustration of an x-ray inspection system, generally designated 100. Inspection system 100 can comprise one or more linear multibeam x-ray source arrays, generally designated 150, that each can comprise a plurality of individual x-ray beam source elements 152. For instance, each of the plurality of individual x-ray beam source elements 152 can be an x-ray focal spot associated with a cathode element, each of which in turn comprises a substrate with a carbon nanotube (CNT) field emission film on an insulating material (e.g. glass or ceramics). Examples of such a field emission cathode formed at least partially from a nanostructure-containing material can be found in U.S. Pat. No. 6,553,096, the disclosure of which is incorporated herein in its entirety.

As shown in FIG. 1, inspection system 100 can comprise a first x-ray source array 150a and a second x-ray source array 150b arranged in an L-shaped array. FIG. 1 illustrates one configuration, for example, in which each of first and second x-ray source arrays 150a and 150b comprises nine individual x-ray beam source elements 152, but it should be recognized by those having skill in the art that any number of individual x-ray beam source elements 152 can be used (e.g., 5, 50, 100, 256, or more source elements per array), and the configuration and spacing of those elements can vary (e.g., a linear array spaced apart by approximately 2 mm), depending on the desired balance between imaging resolution and the cost and size of the system.

Regardless of the specific configuration, inspection system 100 can be configured such that one or more of the plurality of individual x-ray beam source elements 152 can be selectively activated to emit x-ray beams through an object O positioned within an inspection zone, generally designated 115, and towards one or more x-ray detector arrays, generally designated 160. For example, as shown in FIG. 1, inspection system 100 can comprise a first x-ray detector array 160a arranged substantially opposing first x-ray source array 150a and a second x-ray detector array 160b arranged substantially opposing second x-ray source array 150b. As with x-ray source arrays 150, the specific configuration of x-ray detector arrays 160 can be designed to achieve a desired balance between imaging resolution and cost, size, etc. By way of specific example, each of first and second x-ray detector arrays 160a and 160b can comprise a 10 cm detector defining pixel sizes of approximately 0.39 mm, although the length and detector size can vary widely depending on the system requirements.

X-ray beam source elements 152 can be collimated to substantially a fan beam in the x-y plane so that only a narrow slice of the object is illuminated by x-rays for each projection. Such collimation can reduce unintended x-ray flux to x-ray detector arrays 160 from scattered x-ray photons. Further in this regard, in the case of a two or more plane system, x-ray beam source elements 152 can be collimated in a way that the radiation from one plane will not reach the other planes. In this way, the imaging planes can be treated as independent. X-ray detector arrays 160 can be placed substantially in the same plane (x-y) as a corresponding one of x-ray source arrays 150.

In contrast, in one alternative configuration, fan beams can be generated from a subset of x-ray beam source elements 152 simultaneously, and multiple projection images can be obtained through multiplexing x-ray imaging methods. Examples of multiplexing x-ray imaging methods can be found in U.S. Pat. No. 8,155,262 to Zhou et al. and U.S. Pat. No. 8,189,893 to Zhang et al., the disclosures of which are incorporated herein by reference in their entireties. Alternatively, in another configuration, x-ray beam source elements 152 can be configured to project cone beams by collimation, and corresponding x-ray detector arrays 160 can comprise multi-row or area detectors modules.

Figure 2A:
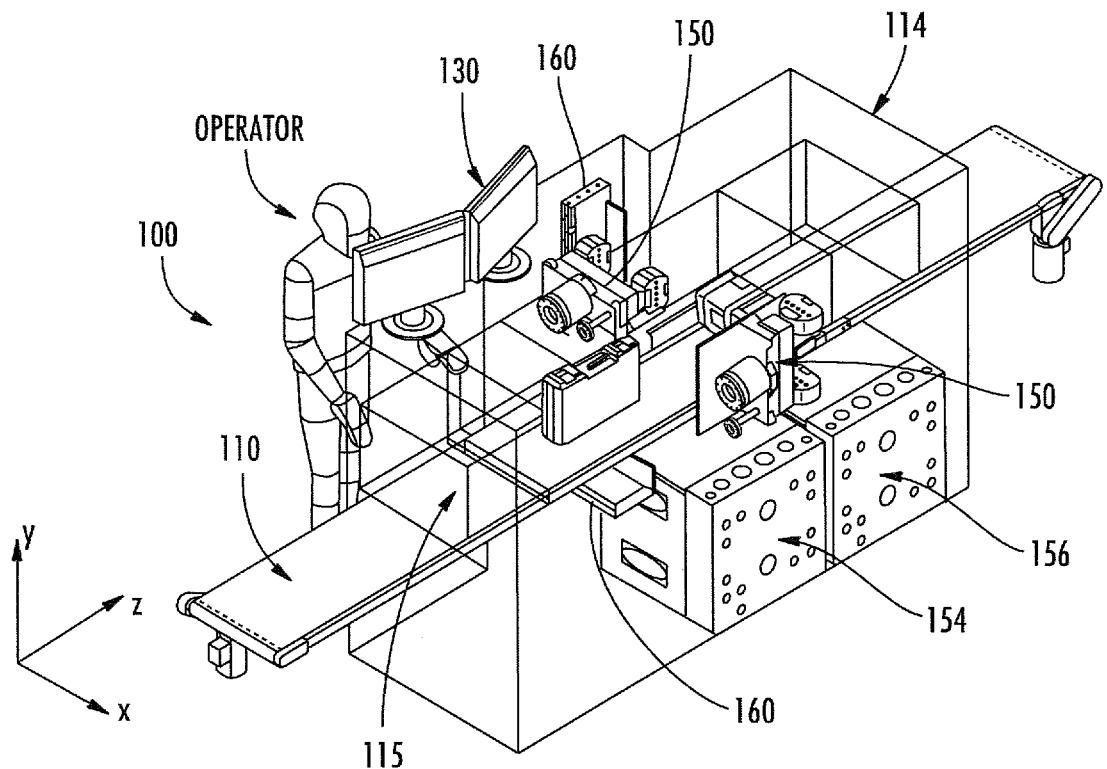
FIG. 2A is a perspective view illustrating an x-ray inspection system according to an embodiment of the presently disclosed subject matter.
Figure 2B:
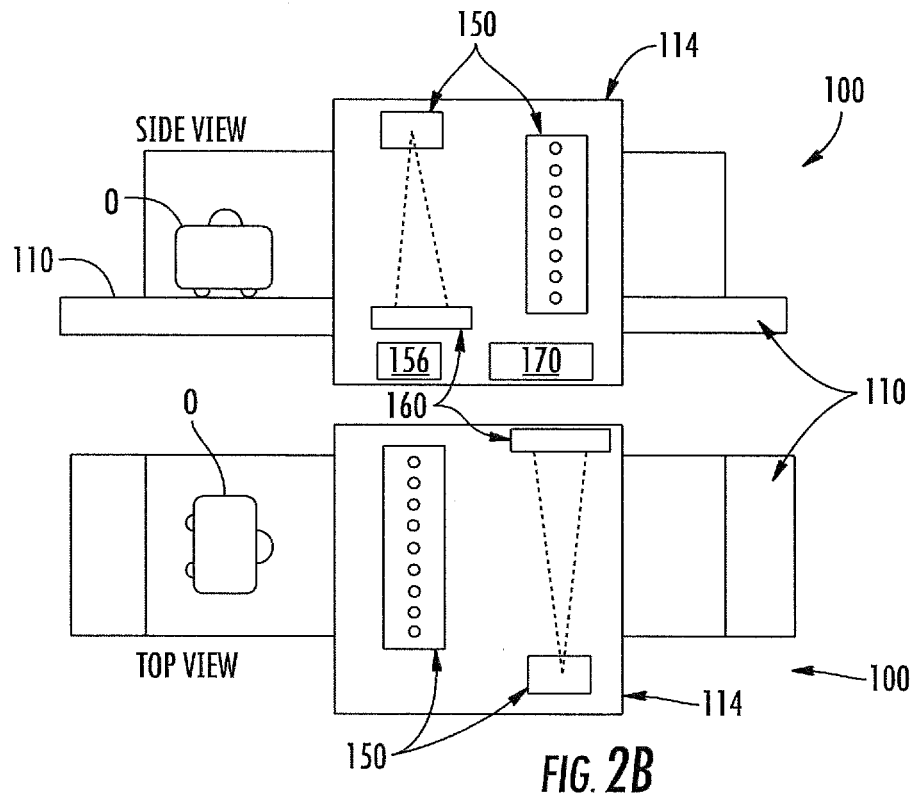
FIGS. 2B and 2C each show side and top views illustrating various configurations of x-ray source arrays in an x-ray inspection system according to embodiments of the presently disclosed subject matter.
Figure 2C:
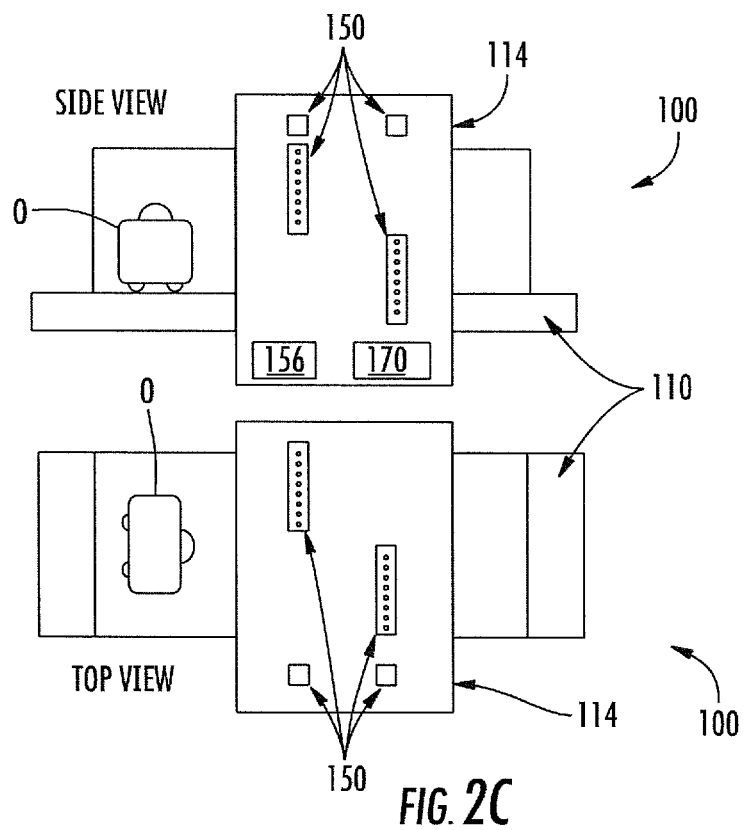

Referring to FIGS. 2A through 2C, it is shown that inspection system 100 can further comprise a conveyor 110 configured to transport objects to be inspected (i.e., airline passenger baggage) into inspection zone 115 along the z-axis of the system. Specifically, inspection zone 115 can be configured as a substantially rectangular transport tunnel through which conveyor 110 passes and about which multiple multibeam x-ray source arrays 150 and x-ray detector arrays 160 can be arranged. Inspection area 115 can be surrounded by a protective housing 114. The elements of x-ray source arrays 150 and detector arrays 160 can be substantially linear so that they can be installed close to the transport tunnel.

A high-voltage (HV) generator 154 can be connected to one or more of x-ray source arrays 150 to provide the anode voltage for x-ray source arrays 150. HV generator 154 can be a single unit that supplies voltage to all of x-ray source arrays 150, or there can be several units configured to supply anode voltage to each of x-ray source arrays 150 independently. An electronic controller 156 can further be connected to one or more of x-ray source arrays 150 to switch individual x-ray beam source elements 152 in x-ray source arrays 150, and such switching can be based on signals from a control system (not shown). The sequence that is used for activating x-ray beam source elements 152 can be stored in electronic controller 156 and can be programmed freely (e.g., to modify pulse length, amplitude) over a network interface (e.g., Ethernet). Electronic controller 156 can also monitor the status of x-ray source arrays 150 and produce warning or error messages that are conveyed in real time to the control system.

Electronic controller 156 can further regulate the x-ray output from x-ray beam source elements 152 (e.g., pulse length and amplitude) such that the output is repeatable from pulse to pulse (i.e., from the same source element) and from source to source (i.e., different source elements). Over time, those having skill in the art will recognize that the output from x-ray beam source elements 152 can degrade slowly and their emission properties can change (e.g., inherent behavior of the CNT field emitters). To address such degradation, electronic controller 156 can monitor the change in the emission process and regulate the emission process in order to maintain a constant output. Electronic controller 156 can then produce a warning message to the control system when the source array approaches the end of its lifetime. This monitoring allows scheduling of maintenance work ahead of time and forecasting when the system will not be available for use.

As discussed above, inspection system 100 can use multiple multibeam x-ray source arrays 150 (e.g., between 2 and 5 arrays), and each of x-ray source arrays 150 can have a plurality of individual x-ray beam source elements 152 (e.g., 30 to 75 individual beams). Even with these multiple source elements, however, each of x-ray source arrays 150 can occupy an amount of space (e.g., a length of 30 cm) that does not diverge greatly from the space required for conventional x-ray systems. X-ray source arrays 150 can be arranged around inspection zone 115 at least on two sides of the tunnel, with x-ray source arrays 150 being arranged in either one or several planes. In fact, x-ray source arrays 150 and x-ray detector arrays 160 can be designed to be mounted in a modular format. Such a modular design can allow for easier maintenance and system modification, as well as easy adaptation of the technology to other tunnel sizes.

Specifically, as shown in FIG. 2B, for example, inspection system 100 can comprise at least two x-ray source arrays 150 arranged across conveyor 110 (i.e. each being positioned such that x-ray beam source elements 152 are arranged in a plane perpendicular to the direction of travel of conveyor 110): one arranged "above" imaging zone 115 (i.e., in a plane opposite imaging zone 115 from conveyor 110) and another arranged to a side of imaging zone 115 (i.e., in a plane perpendicular to conveyor 110). In addition, the one or more x-ray source arrays 150 can be positioned on two parallel planes separated by a predetermined distance along the direction of travel of conveyor 110 so that they obtain images of an object O traveling along conveyor 110 in a substantially sequential manner. In this way, the one or more x-ray source arrays 150 can be used to obtain projection images of object O from different viewing angles as it travels along conveyor 110 without mechanical motion of the arrays and with the potential for faster image acquisition speed.

Alternatively, as shown in FIG. 2C, for example, additional x-ray source arrays 150 can be arranged about imaging zone 115 to provide imaging from even more viewing angles. Specifically, two x-ray source arrays 150 can be arranged above imaging zone 115, with one positioned over one half of conveyor 110 (e.g., a left half) and the other positioned over another half of conveyor 110 (e.g., a right half). Two more of x-ray sources 150 can be arranged to a side of imaging zone 115, with one positioned nearer to conveyor 110 than the other (i.e., one in a "low" position and the other in a "high" position). Those having skill in the art will recognize, however, that many further variations in the number and positioning of x-ray source arrays 150 can be used to further improve imaging speed and resolution.

In yet a further alternative configuration, x-ray source array 150 can be positioned such that x-ray beam source elements 152 are arranged along a line along the direction of travel of conveyor 110, whereas x-ray detector array 160 can be positioned along a line substantially perpendicular to the direction of travel. Alternatively, x-ray source array 150 can be positioned substantially perpendicular to the direction of travel of conveyor 110, and x-ray detector array 160 can be positioned substantially parallel to the direction of travel. In either arrangement, a single set of substantially linear components can be used to scan object O from multiple viewing angles in three dimensions.

In any arrangement, a method for operating inspection system 100 can comprise all x-ray beam source elements 152 being scanned in a sequential manner. In particular, for example, all x-ray beam source elements 152 from a first of x-ray source arrays 150 can be activated (e.g., from first to last within the array), and then all x-ray source elements from a second of x-ray source arrays 150 can be activated, and so on, starting with those x-ray beam source elements 152 arranged in a first plane (e.g., the left-most/forward plane in FIG. 2B or 2C) and then going to a second plane (e.g., the right-most/rearward plane in FIG. 2B or 2C). The total scan time per slice (e.g., full cycle) can be given by the detector processing time multiplied by the total number of views. Because the planes in such a system can be independent, they can be run in a parallel way that reduces the total scan time per slice by the number of planes scanned in parallel. In this case, the power requirement for the anode power supply (e.g., HV generator 154) can be the power of a single plane multiplied by the number of planes, thus increasing the cost of the power supply but also increasing the achievable object throughput for a given z-resolution.

Regardless of the specific arrangement and configuration of x-ray source arrays 150, an image reconstruction method can be used to translate the output of x-ray detector arrays 160 into high resolution 3D images. For example, a software-implemented algorithm can be based on the total variation (TV) method iterative reconstruction algorithm published by Dr. Pan. (See, e.g., Sidky and Pan, Phys. Med. Biol. 53 (2008) 4777) Such an algorithm can be used to reconstruct 3D image data from a much smaller number of projections than traditional CT and can compensate for missing and truncated data (i.e., three-dimensional tomographic images of the object can be reconstructed even if a certain number of projection images are excluded from the data set for reconstruction). For instance, the probability of detection (PD) and probability of false alarm (PFA) theoretically will not move much for some percentage of missing projections, and thus a proportion of projection images can be excluded without substantially affecting the practical accuracy of the reconstruction. Further in this regard, inspection system 100 can be designed to obtain more projection images than are needed to generate a usable to reconstruct 3D image data to allow for future failure of a limited number of source elements. In addition, the algorithm can work with non-standard x-ray tube and detector geometries. Conventional analytical methods (e.g. Filtered Back Projection) typically need 700-1000 projections with full object coverage. Iterative algorithms only require a fraction of the number of projections (e.g., 70-150 depending upon the application) even with limited angular coverage.

Figure 3:
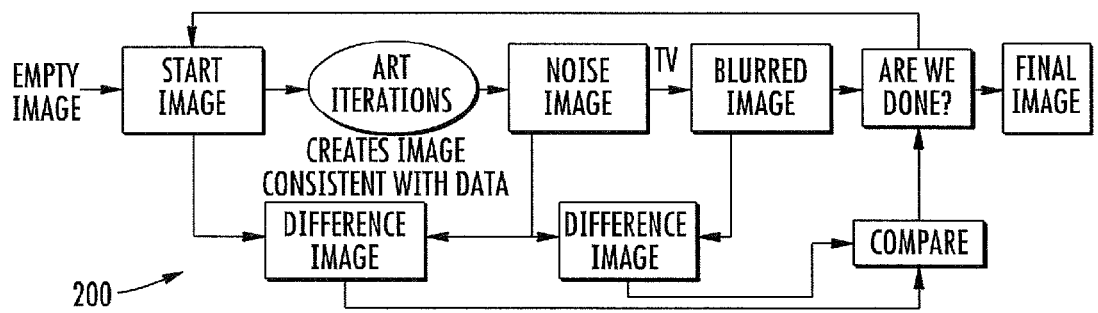
FIG. 3 is a flow diagram illustrating an imaging algorithm for use with an x-ray inspection system according to an embodiment of the presently disclosed subject matter.

A high level flow diagram of a method 200 incorporating such an algorithm is shown in FIG. 3. Method 200 can start with an empty image. An algebraic reconstruction technique (ART) can create an image that is consistent with the measured projection data. This image has high variation interpreted as a "noisy image," which a subsequent TV iteration can smooth so that a "blurred image" is created. The "blurred image" can be the image estimate in the next iteration. The balance between the image accuracy imposed by the ART and the noise suppression added by the TV can be adaptively determined using the difference images.

Because these iterative reconstruction algorithms are more computationally intensive than standard filtered back projection algorithms, they can be run on GPUs to generate almost real time 3D images for threat detection. In this way, method 200 can be used to generate images with a processing time on the order of a few seconds, which allows for automated threat detection at a carry-on baggage checkpoint or in a checked baggage application.

Figure 4:
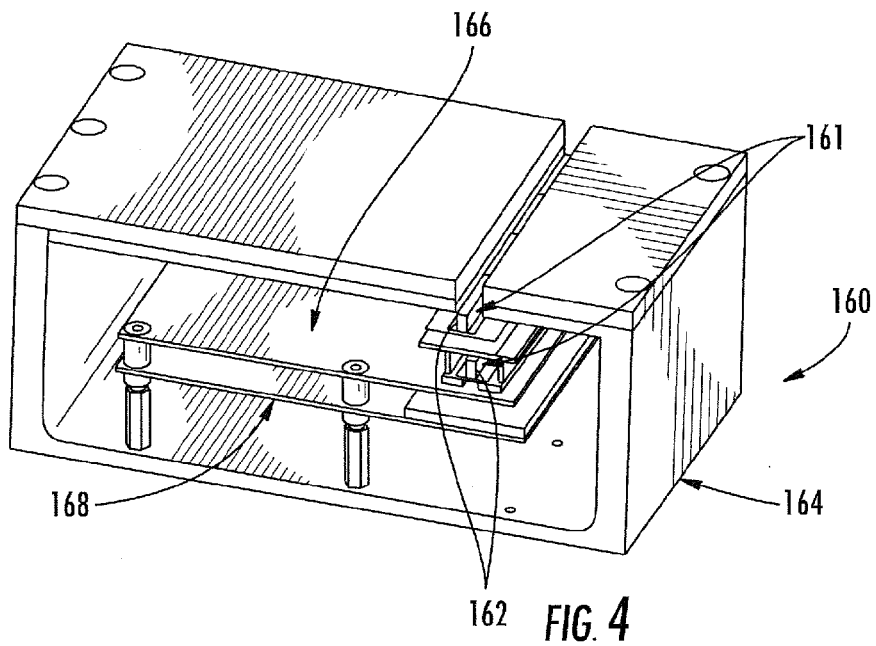
FIG. 4 is a perspective view illustrating an x-ray detector for use in an x-ray inspection system according to an embodiment of the presently disclosed subject matter.

With respect to the specific configuration of x-ray detector arrays 160, FIG. 4 illustrates one arrangement in which photodiodes with scintillators or solid state direct conversion are used. As shown in FIG. 4, each of x-ray detector arrays 160 can comprise multiple scintillators 161 coupled to multiple corresponding photodiodes 162, which can be arranged in either single- or multiple-line configurations. In addition, the multiple scintillators 161 can be configured to measure the x-ray signal at two or more energy levels. Scintillators 161 can for example be chosen from the group of cesium iodide (CsI), Gd2O2S:Tb (Gadox), Gadolinium Oxysulfide (GOS), Cadmium tungstate (CdWO4), or other similar materials known to those having skill in the art. It can be desirable for scintillators 161 to exhibit a short decay time with good light output.

X-ray detector arrays 160 can further comprise electronics associated with photodiodes 162. For example, as shown in FIG. 4, x-ray detector arrays 160 can comprise one or more head board 166, and some modules can also contain a signal processing board (SPB) 168 for data readout. For material discrimination, x-ray detector arrays 160 can be configured for collecting x-ray signal from at least 2 different x-ray spectra. Scintillators 161 can be arranged in a stacked configuration, with a comparatively lower energy spectrum being measured by a top module and a comparatively higher energy spectrum being measured by a bottom module as shown in FIG. 4. Alternatively or in addition, the components can be arranged in a parallel configuration, with scintillators 161 placed side-by-side, and/or multiple lines of scintillators 161 (i.e., multi-row or area detector modules) can be used to speed up the data acquisition process. Different x-ray spectra can be created by adding a filter material in front of one of scintillators 161, shifting the mean energy of the x-ray photons to higher energies. A further alternative configuration can involve computing a third spectrum from the linear combination of the two existing spectra and also computing a third detector signal from the linear combination of the two measured ones. In yet a further alternative, the x-ray energy can be modulated by changing the acceleration voltage for different projection views. For example, x-ray source arrays 150 can comprise a first x-ray source array operable to generate relatively lower energy x-ray beams and a second x-ray source array operable to generate relatively higher energy x-ray beams.

The detector processing time can typically be determined by the number of SPBs 168 available to read the information from the individual detector head boards. Inspection system 100 can use multiple detector arrays 160 (and thus multiple SPBs 168) such that the signal from the previous pulse is read out while it is integrating over the next pulse and so on. In this way, there is no additional time required for the integration. Using a higher number of SPBs 168 can increase the system cost, but it can also reduce processing time as long as a minimum x-ray dose can be obtained for each projection. The minimum time is therefore determined either by the pulse length or the achievable processing time of SPBs 168.

There are schemes, however, to reduce system cost (e.g., detector and anode power supply) while minimizing the time per view for multi-plane systems. In the case of a two plane system (See, e.g., FIGS. 2B and 2C), the processing time per SPB 168 can be chosen to be two times the x-ray pulse length. For instance, in the case of a 100 µs x-ray pulse, the processing time can be approximately 200 µs. The required processing time in SPB 168 per head board 166 can be on the order of approximately 50 µs, which allows up to four of head boards 166 to be processed with a single SPB 168. During the time where the x-ray pulse is off in the first plane, one of x-ray source arrays 150 in the second plane can be pulsed (i.e., time offset) and the corresponding one of x-ray detector arrays 160 can be read. This means that only 50% of the SPBs 168 need be used, and only one of x-ray source arrays 150 is on at the same time, which can also reduce the power requirement for HV generator 154.

In this scheme, the tube duty cycle per plane is only 50%. With several tubes per plane, the duty cycle for the individual tube is 1/(# planes×# tubes per plane), which directly reduces the mean power per tube for the source. The achievable mean power is usually limited in x-ray tubes due to the very inefficient way the x-rays are produced (e.g., 99% of the electron energy is converted into heat and the rest into useful x-ray radiation).

In each readout cycle, data from head boards 166 can be transferred to data processor 170, which stores the data for further processing. The raw data can be processed to remove detector artifacts (e.g., gain correction, offset correction), and the projection data can be transferred to the reconstruction algorithm that calculates the individual slices that together form a 3D data set. 3D images from all energy bins can be reconstructed with an iterative reconstruction algorithm in real-time (e.g. using the TV algorithm implemented in method 200 or a modified TV algorithm like the edge-preserving algorithm reported by Z. Tian et al, Phys. Med. Biol. 56 (2011) 5949). Iterative reconstruction is computationally extensive, however, so in order to achieve short reconstruction times, the chosen reconstruction algorithm can be implemented in parallel code on one or more GPUs.

Figure 5A:
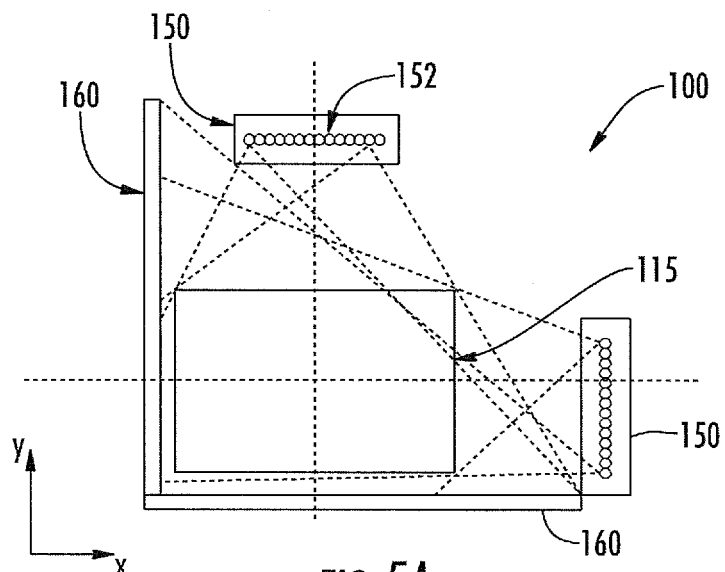
FIGS. 5A through 5O are schematic diagrams illustrating various configurations for x-ray source arrays and x-ray detectors of an x-ray inspection system according to embodiments of the presently disclosed subject matter.
Figure 5B:
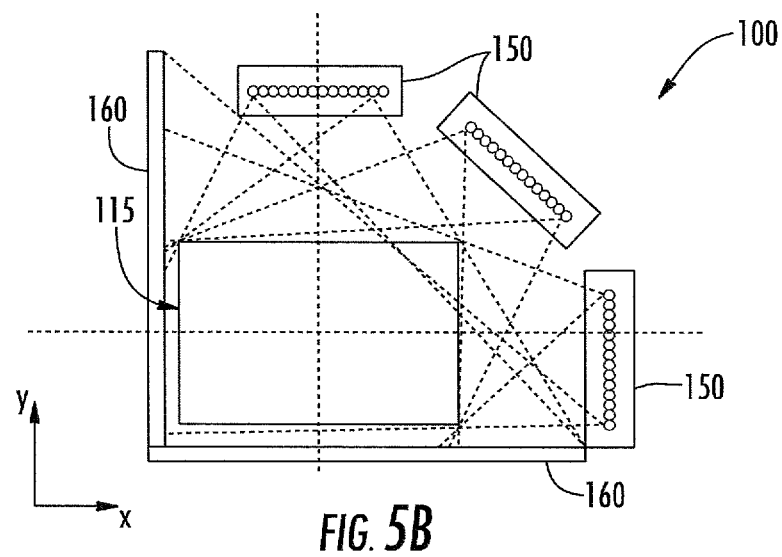
Figure 5C:
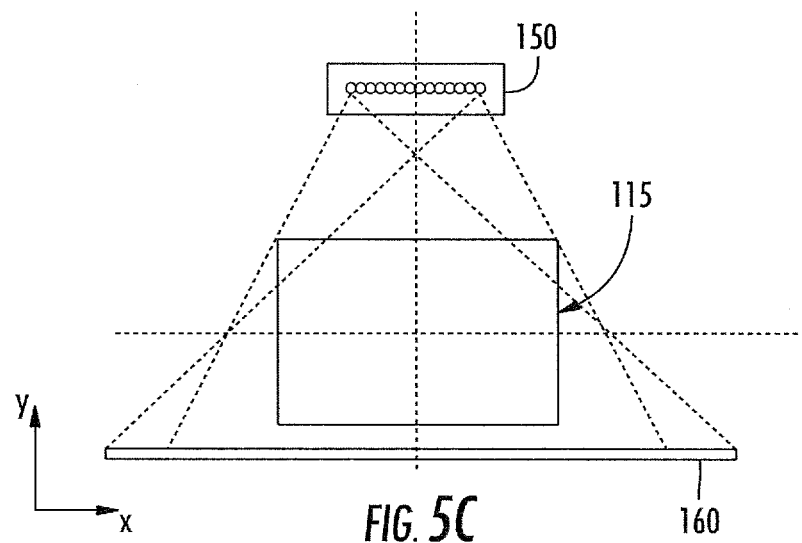
Figure 5D:
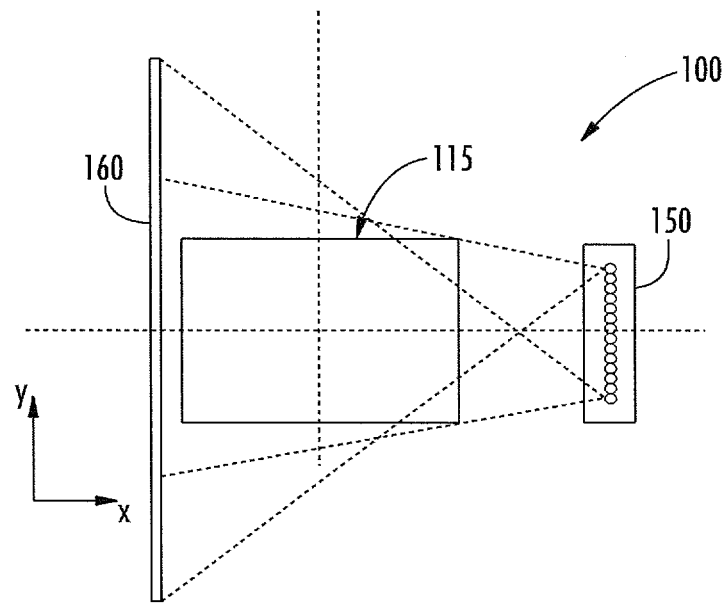
Figure 5E:
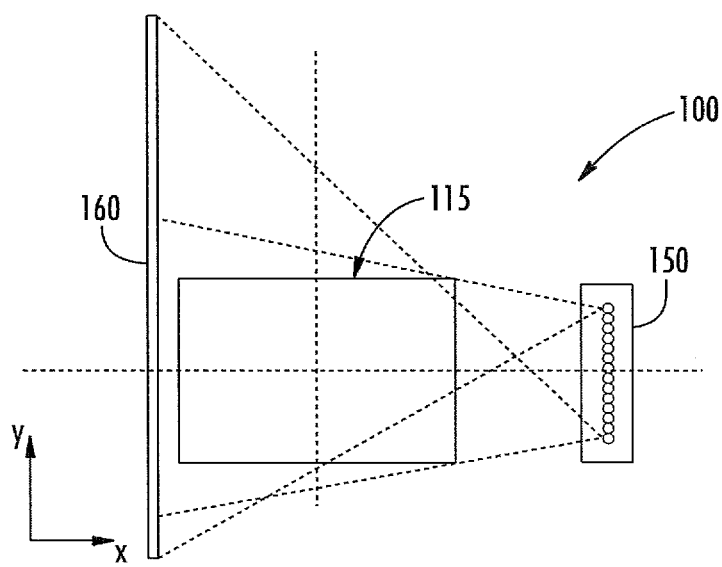
Figure 5F:
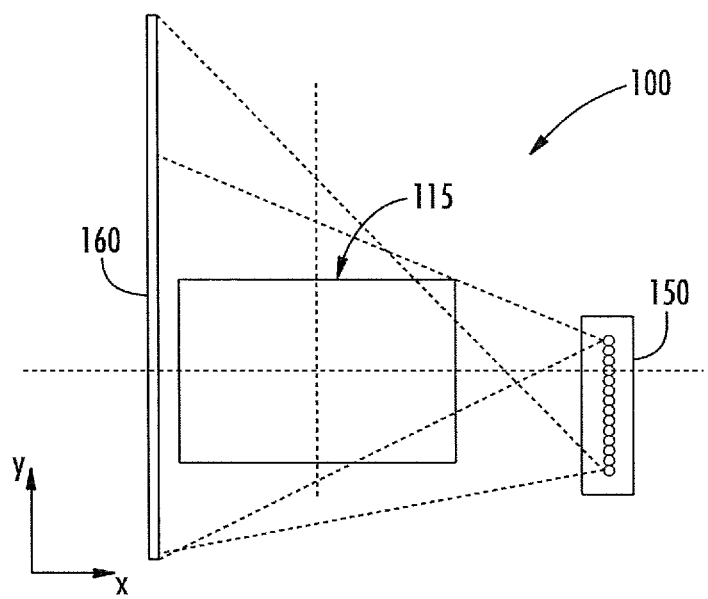
Figure 5G:
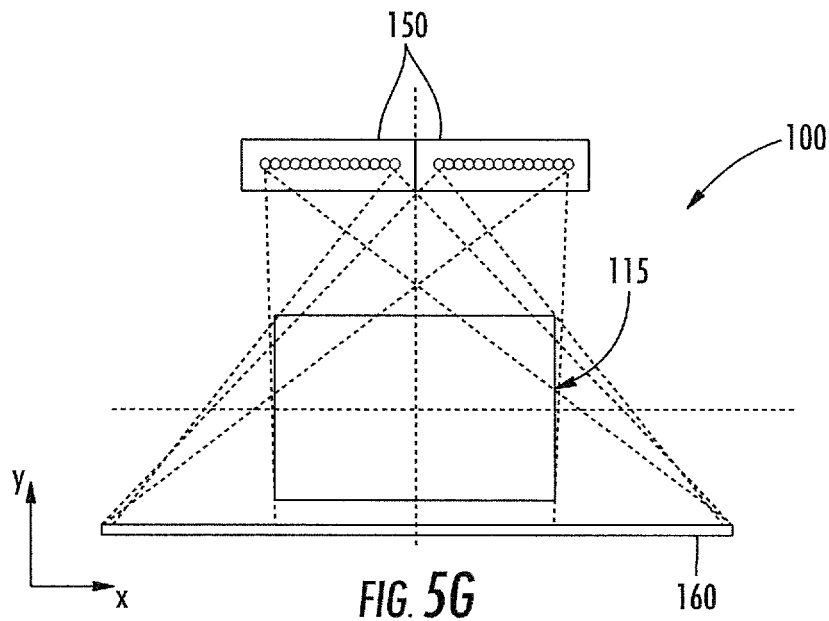
Figure 5H:
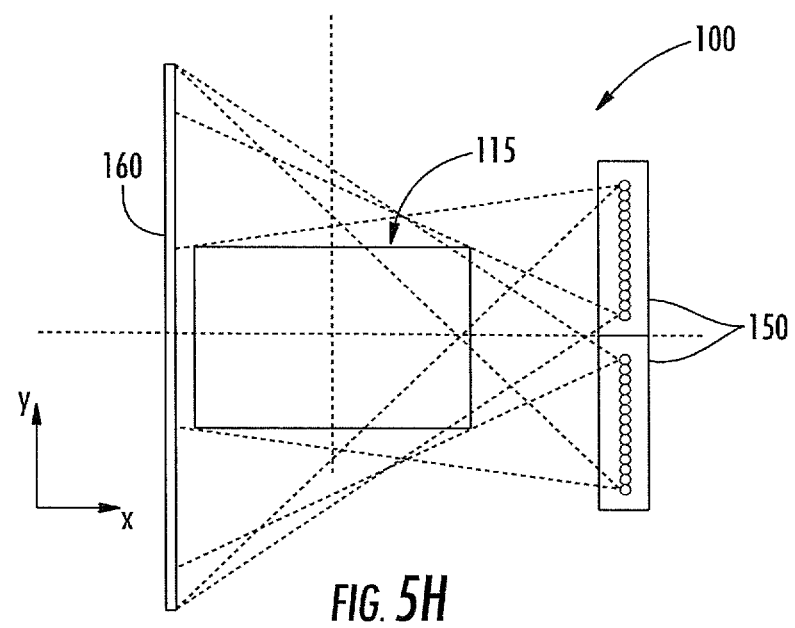
Figure 5I:
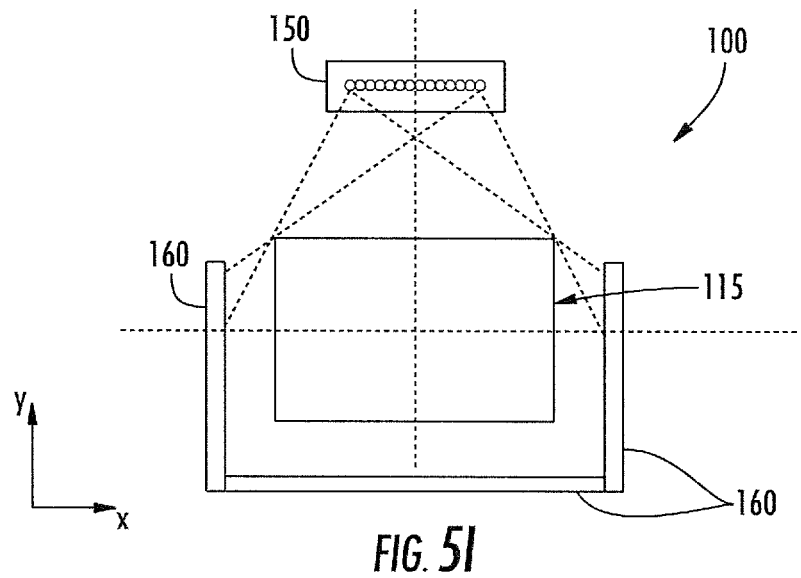
Figure 5J:
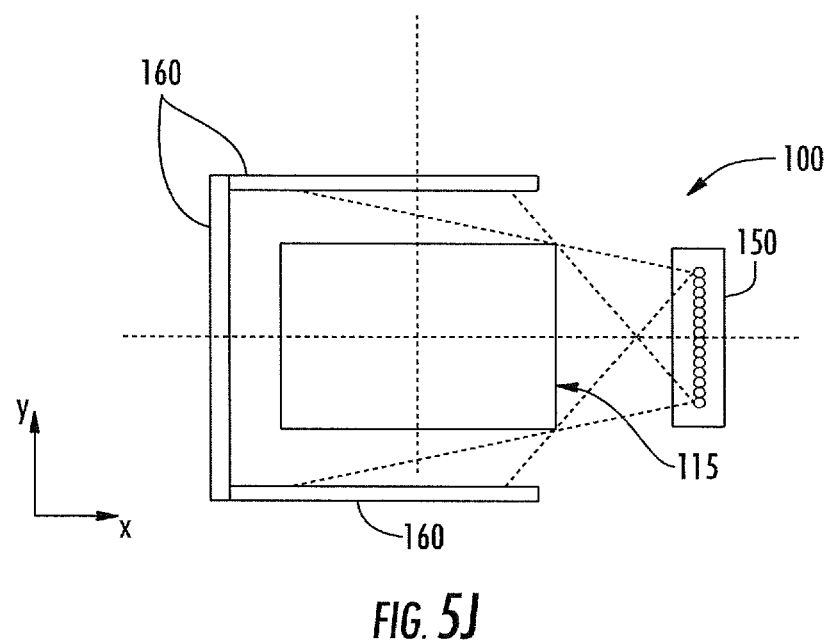
Figure 5K:
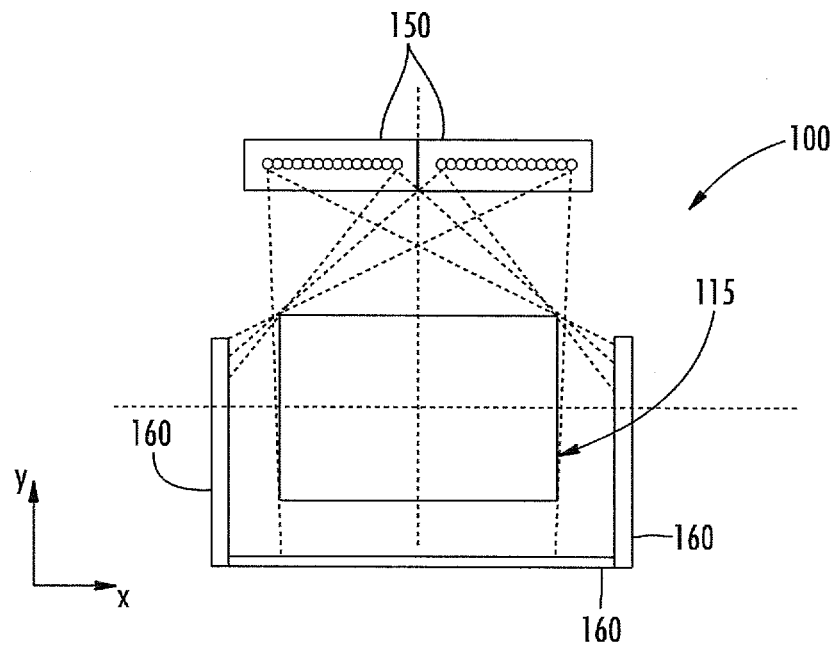
Figure 5L:
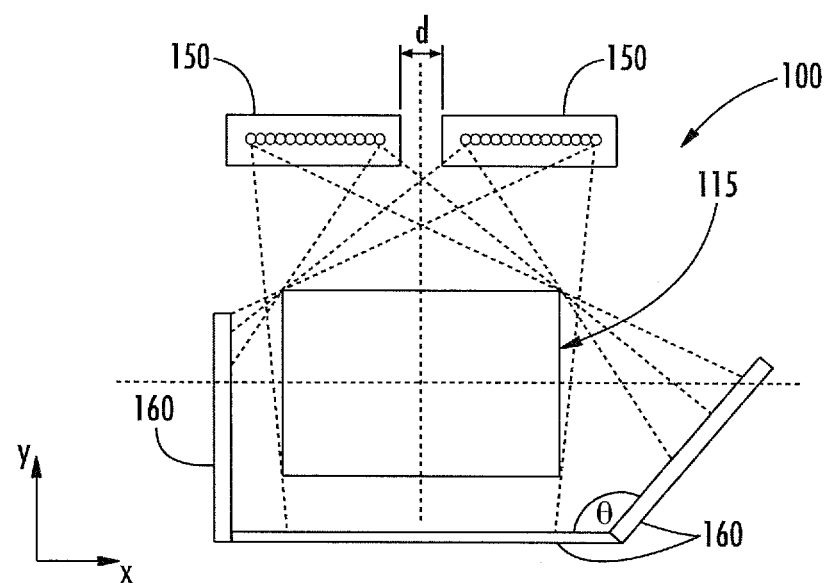
Figure 5M:
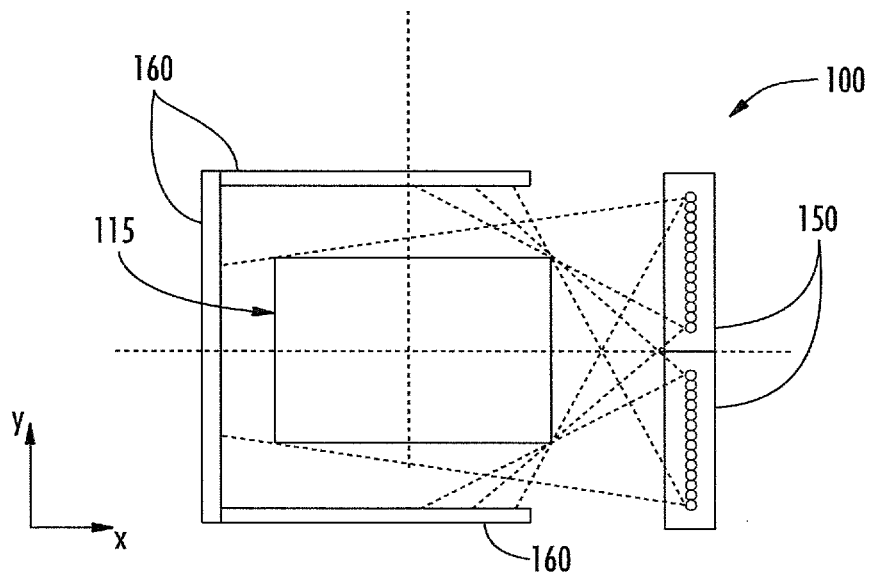
Figure 5N:
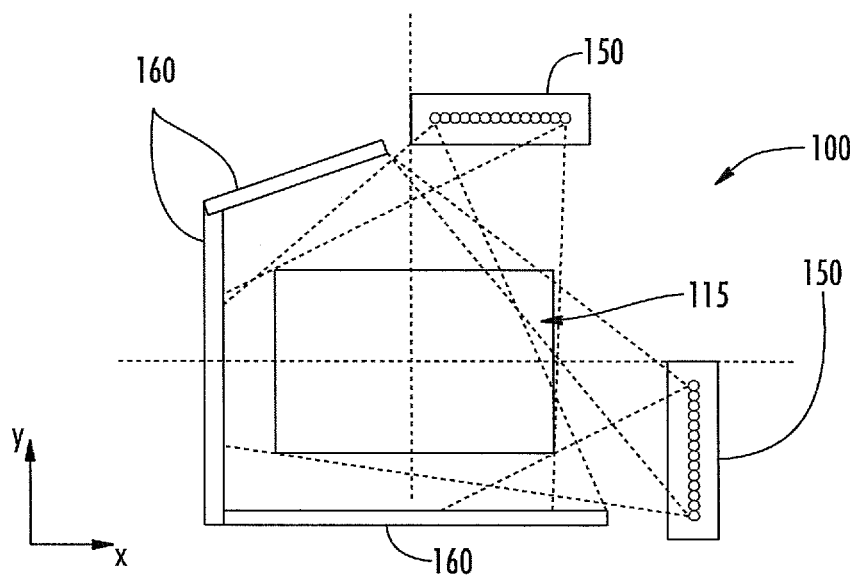
Figure 5D:
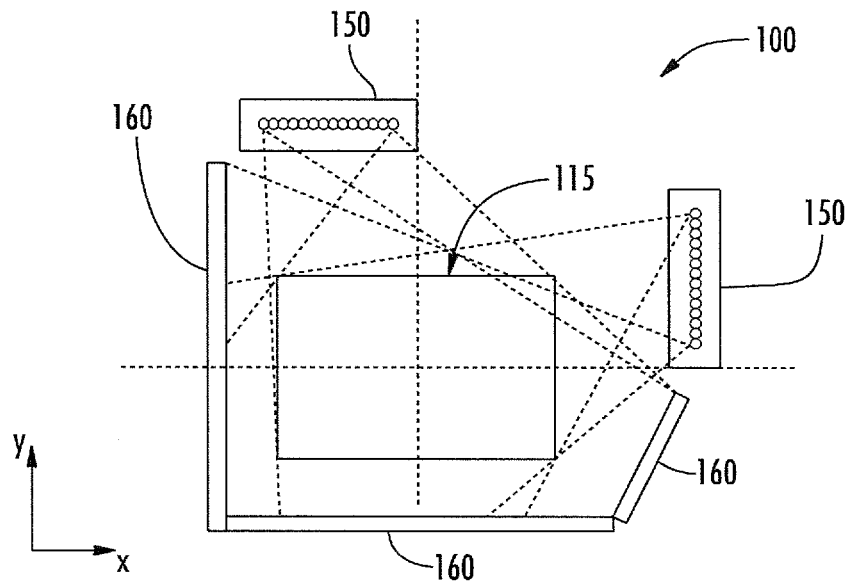
Figure 6:
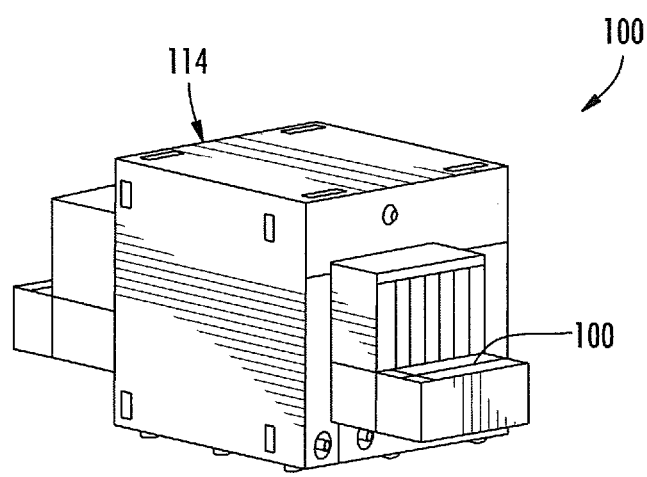
FIG. 6 is a perspective view illustrating an x-ray inspection system according to an embodiment of the presently disclosed subject matter.

Referring again to FIGS. 2B and 2C, various configurations for x-ray source arrays 150 and detector arrays 160 are shown. Those having ordinary skill in the art will recognize, however, that due to the modularity of the x-ray source arrays and also the detector arrays a large number of suitable source and detector configurations are possible. Some possible configurations are shown in FIGS. 5A through 5O, for example, including various combinations of one or more x-ray source arrays 150 and one or more corresponding x-ray detector arrays 160 arranged in straight, L-shaped, U-shaped, and other configurations. The configurations shown in FIGS. 5A through 5O only show exemplary configurations, and the number and relative positioning of x-ray source arrays 150 and x-ray detector arrays 160 can be modified based on the particular desired parameters for a given implementation of inspection system 100. For example, as shown in FIG. 5L, some of the parameters of inspection system 100 that can be adjusted can comprise a distance d between adjacent x-ray source arrays 150 and an angle θ between x-ray detector arrays 160. In addition, the configurations shown in FIGS. 5A through 5O only show exemplary configurations using linear x-ray tubes, but curved multibeam x-ray tubes can also be used with curved detectors or linear detectors, and curved multibeam x-ray tubes have been built.

In general, data truncation on x-ray detector arrays 150, limited angular coverage, and missing projections can lead to artifacts in the reconstructed data. As a result, the arrangement of components can be selected to minimize these factors to the extent possible. As shown in each of the exemplary configurations, for example, since the length of the detector can determine how much of the projection information is captured, it can be desirable for one or more of x-ray detectors 160 to be positioned to cover at least one side of imaging zone 115 with a length that can be longer than the tunnel dimension. For further coverage, x-ray detectors 160 can cover as much of the tunnel circumference as possible on up to three sides (e.g., sides can have partial coverage) of imaging zone 115. The positions of x-ray source arrays 150 can determine the angular coverage, as gaps between x-ray source arrays 150 can lead to missing projections. The configurations shown in FIGS. 5A through 5O can be used either in single plane or multi-plane configurations.

Regardless of the specific configuration of the components therein, inspection system 100 can be designed to have an overall shape and size that is comparable to typical CT scanners. Similar to existing multiview systems, however, the shape of inspection system 100 can be substantially rectangular because stationary linear multibeam tubes are used instead of a circular gantry. As a result of this compact, non-circular shape, inspection system 100 can comprise a system footprint that is equal to or smaller than standard multiview non-CT system. Inspection system 100 can thus easily fall within the TSA space requirements, allowing room on either side for maintenance access.

Experimental Data

Figure 7:
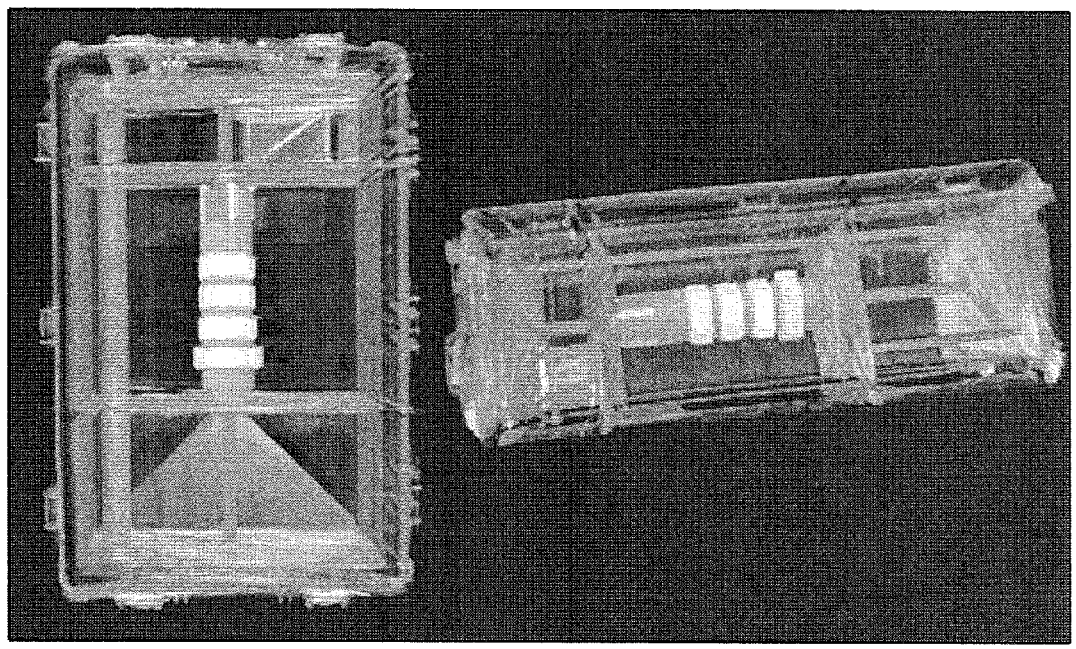
FIG. 7 shows images of an Article A NIST phantom taken using an x-ray inspection system according to an embodiment of the presently disclosed subject matter.

FIG. 7 shows two different 3D images of an Article A NIST phantom taken using inspection system 100. The Article A NIST phantom is an industry standard phantom for quantifying image quality. The initial reconstruction of this phantom demonstrates the spatial resolution of non-circular geometry since the small metal pins, acetal fan, and metal rings are immediately identifiable. Also, the detail in the hinges and handles on the side demonstrate the system resolution away from the center. In fact, preliminary calculations performed utilizing this phantom show good CT number stability from slice to slice, indicating the accuracy and stability of the reconstruction algorithm with a non-circular scanner.

Figure 8:
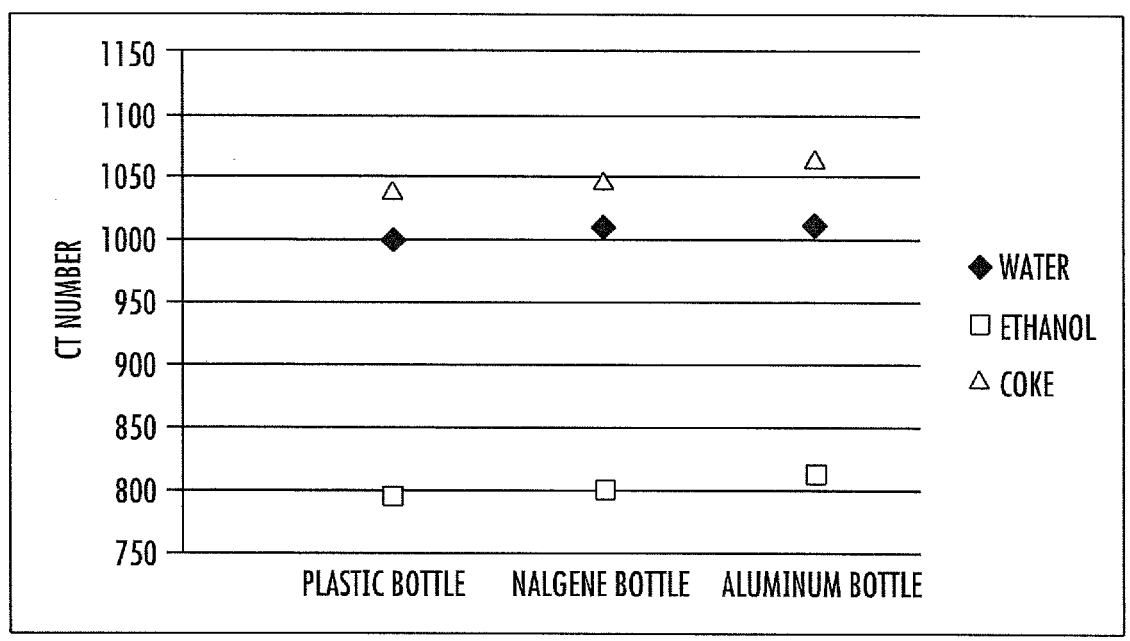
FIG. 8 is a chart illustrating the mean CT number calculated for three different liquids in different types of bottles using an x-ray inspection system according to an embodiment of the presently disclosed subject matter.

One advantageous feature of inspection system 100 is the ability to image bottles containing liquids that are inside carry-on bags. The graph shown in FIG. 8 plots the mean CT number calculated for three different liquids in different types of bottles. For each calculation, the bottles were filled with one of the liquids and placed in a 22 inch carry-on bag filled with clothing. Despite the scatter from the bags and the different types of bottles, there is less than 2% difference in the mean CT number for each liquid. This difference is less than the relative difference in mean CT numbers between two very similar liquids (coke and water), and demonstrates that inspection system 100 is capable of imaging and identifying liquids. The ability to differentiate between similar liquids and the system's high resolution provides the ability to identify liquids in small bottles (e.g., as small as 3 ounces or less).

Figure 9:
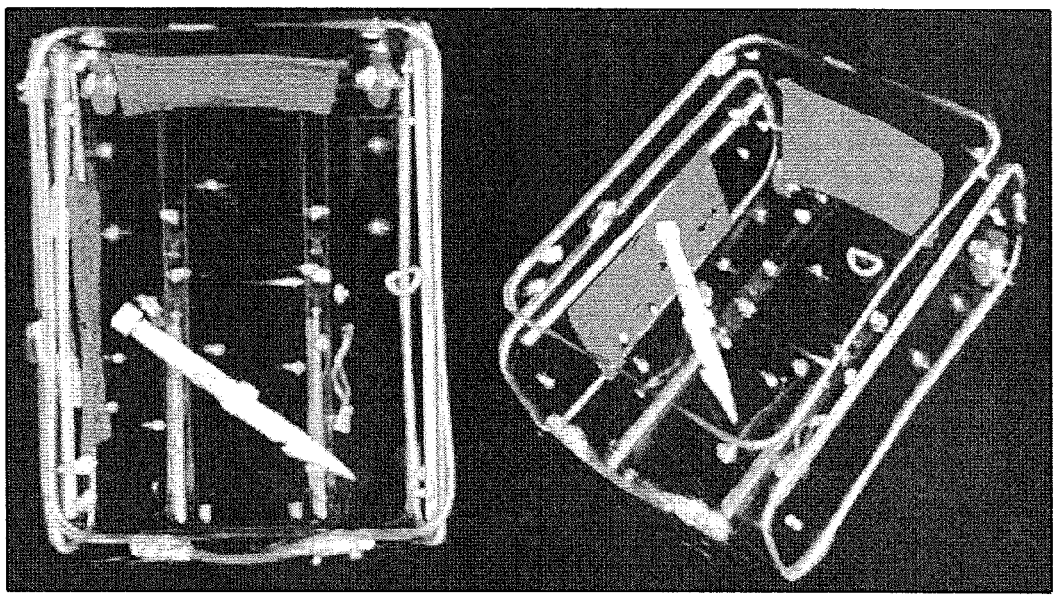
FIG. 9 shows two different views from three dimensional x-ray images of a 22 inch carry-on bag with two thin rubber sheets highlighted in red plus a large dive knife obtained using an x-ray inspection system according to an embodiment of the presently disclosed subject matter.

In addition, due to the fast switching of x-ray beam source elements 152 (e.g., CNT multibeam x-ray emitters), inspection system 100 is able to generate very narrow reconstruction slices resulting in a very high resolution in the Z direction. This high resolution from a voxel size of approximately 1.5 mm in the Z direction enables visualization and analysis of sheet materials in any orientation, which is a feature that is not available in any other CT system at the required throughput rate. FIG. 9 shows two different views from three dimensional x-ray images of a 22 inch carry-on bag with two thin rubber sheets highlighted in red plus a large dive knife. Two views are shown: the first is a top-down view with the bottom of the bag sitting on the belt, and the second is a tilted view to demonstrate a 3-D perspective. This bag was scanned with both thin sheets perpendicular to the belt, and the image was reconstructed with 1.5 mm isotropic voxels. The rubber sheets were placed along the edges of the interior of the bag, which was filled with clothing. The rubber sheets have material properties close to certain threats and demonstrate the high resolution capability of inspection system 100 and its potential for identifying threats.

The thin rubber sheets make it easy to observe that the scanner not only resolves the sheets but also the shape and contour of the sheets. The dive knife is clearly visible with details such as a notch in the blade, a latch for the sheath, and the weight at the end of the handle. The 3-D perspective image demonstrates that x-rays have penetrated through the knife and imaged the objects beneath it. A global threshold was applied to these images to remove the clothing and other low density materials, but denser objects such as zippers and buttons remain visible. The frame of the bag, wheels, and handle also remain visible since these are also made from denser materials.

This detection of thin sheet materials as well as the analysis of liquids in bottles contained within a carry-on bag shows the potential of the system to automatically detect threats in the bag at the checkpoint. This capability exists advantageously also without the need for specialized ancillary equipment.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter. While the subject matter herein has been has been described in reference to specific aspects, features, and/or illustrative embodiments, the utility of the described subject matter is not thus limited, but rather extends to and encompasses numerous other variations, modifications and alternative embodiments, as will suggest themselves to those of ordinary skill in the field of the present subject matter, based on the disclosure herein. Various combinations and sub-combinations of the structures and features described herein are contemplated and will be apparent to a skilled person having knowledge of this disclosure. Any of the various features and elements as disclosed herein may be combined with one or more other disclosed features and elements unless indicated to the contrary herein. Correspondingly, the subject matter as hereinafter claimed is intended to be broadly construed and interpreted, as including all such variations, modifications and alternative embodiments, within its scope and including equivalents of the claims.

What is claimed is:

1. A computed tomography inspection system, comprising:
    a conveyor configured to move an object to be inspected through an inspection zone along a direction of travel;
    one or more multibeam x-ray source arrays operable to provide multiple collimated x-ray beams through the inspection zone along a direction substantially perpendicular to the direction of travel;
    one or more x-ray detector arrays configured to detect x-ray beams passing through the inspection zone from the x-ray source array;
    an electronic controller operable to electronically turn on and turn off individual x-ray beams from the x-ray source array according to a preprogrammed pattern;
    a signal processing unit operable to record corresponding x-ray signals detected by the x-ray detector array and to form multiple x-ray projection images of the object; and
    a data processor unit operable for processing the multiple x-ray projection images into three-dimensional tomographic images of the object.

2. The inspection system of claim 1, wherein the inspection zone comprises a tunnel through which the conveyor passes.

3. The inspection system of claim 1, wherein the one or more multibeam x-ray source arrays comprise one or more non-circular arrays.

4. The inspection system of claim 1, wherein the one or more multibeam x-ray source arrays are configured to generate multiple collimated x-ray fan beams.

5. The inspection system of claim 1, wherein the one or more multibeam x-ray source arrays are configured to generate multiple collimated x-ray cone beams.

6. The inspection system of claim 1, wherein each of the one or more multibeam x-ray source arrays comprises a plurality of field emission electron sources.

7. The inspection system of claim 6, wherein each of the plurality of field emission electron sources comprises carbon nanotube field emission electron sources.

8. The inspection system of claim 1, wherein one or more first multibeam x-ray source arrays are disposed above or below the inspection zone and one or more second multibeam detector arrays are disposed at a side of the inspection zone.

9. The inspection system of claim 1, wherein each of the one or more multibeam x-ray source arrays comprises between approximately 5 and 100 individual x-ray generating source elements.

10. The inspection system of claim 1, wherein the one or more x-ray source arrays comprise a first x-ray source array operable to generate relatively lower energy x-ray beams and a second x-ray source array operable to generate relatively higher energy x-ray beams.

11. The inspection system of claim 1, wherein one of the one or more multibeam x-ray source arrays and a corresponding one of the one or more x-ray detector arrays are positioned at least substantially in the same plane.

12. The inspection system of claim 1, wherein the one or more multibeam x-ray source arrays comprise at least one first multibeam x-ray source array and at least one second multibeam x-ray source array;
    wherein the one or more x-ray detector arrays comprise at least one first x-ray detector array corresponding to the first multibeam x-ray source array and at least one second x-ray detector array corresponding to the second multibeam x-ray source array; and
    wherein the first multibeam x-ray source array and the second multibeam x-ray source array are positioned on two parallel planes separated by a predetermined distance along the direction of travel.

13. The inspection system of claim 1, wherein the one or more x-ray detector arrays comprise one of an L-shaped array or a U-shaped array.

14. The inspection system of claim 1, wherein the one or more x-ray detector arrays each comprise at least two sets of detecting elements, wherein one set is optimized to detect relatively lower energy x-ray and another set is optimized to detect relatively higher energy x-ray.

15. The inspection system of claim 1, wherein the one or more x-ray detector arrays comprise multiple detector lines or an area detector.

16. The inspection system of claim 1, wherein the data processing unit is configured and operable such that three-dimensional tomographic images of the object can be reconstructed when a subset of projection images are excluded from the data set for reconstruction.

17. A method for x-ray inspection of objects, the method comprising:
    moving an object to be inspected through an inspection zone along a direction of travel;
    operating one or more multibeam x-ray source arrays to provide multiple collimated x-ray beams through the inspection zone along a direction substantially perpendicular to the direction of travel;

electronically turning on and turning off individual x-ray beams from the x-ray source array according to a pre-programmed pattern;

detecting x-ray beams passing through the inspection zone from the x-ray source array;

recording corresponding x-ray signals detected by the x-ray detector array and to form multiple x-ray projection images of the object; and processing the multiple x-ray projection images into three-dimensional tomographic images of the object.

18. The method of claim 17, wherein recording corresponding x-ray signals comprise recording a total number of projections that is less than approximately 200.

19. The method of claim 17, wherein processing the multiple x-ray projection images comprises utilizing iterative reconstruction algorithms.

20. The method of claim 17, wherein operating one or more multibeam x-ray source arrays comprises generating fan beams from a subset of x-ray source elements simultaneously; and wherein recording corresponding x-ray signals comprises obtaining multiple projection images through multiplexing x-ray imaging methods.

* * * * *